(12) United States Patent
Choi et al.

(10) Patent No.: US 9,913,867 B2
(45) Date of Patent: Mar. 13, 2018

(54) **COMPOSITION COMPRISING EXTRACT OF MIXTURE OF *UNDARIA PINNATIFIDA* SPOROPHYLLS AND ASCIDIAN SHELLS FOR TREATING ATOPIC DERMATITIS**

(71) Applicant: INDUSTRY-ACADEMIC COOPERATION FOUNDATION GYEONGSANG NATIONAL UNIVERSITY, Gyeongsangnam-do (KR)

(72) Inventors: Beyong-dae Choi, Gyeongsangnam-do (KR); Seong-hun Jeong, Gyeongsangnam-do (KR); Shi-hyang Park, Gyeongsangnam-do (KR); Myung-sook Kim, Busan (KR); Soon-ok Choi, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 353 days.

(21) Appl. No.: 14/402,302

(22) PCT Filed: Oct. 31, 2012

(86) PCT No.: PCT/KR2012/009070
§ 371 (c)(1),
(2) Date: Nov. 19, 2014

(87) PCT Pub. No.: WO2013/176351
PCT Pub. Date: Nov. 28, 2013

(65) Prior Publication Data
US 2015/0140112 A1 May 21, 2015

(30) Foreign Application Priority Data
May 22, 2012 (KR) ........................ 10-2012-0054488

(51) Int. Cl.
| | | |
|---|---|---|
| *A61K 35/12* | (2015.01) | |
| *A61K 36/02* | (2006.01) | |
| *A61K 36/05* | (2006.01) | |
| *A61K 36/03* | (2006.01) | |
| *A61K 8/97* | (2017.01) | |
| *A61K 8/98* | (2006.01) | |
| *A61K 9/00* | (2006.01) | |
| *A61Q 19/00* | (2006.01) | |
| *A61K 47/46* | (2006.01) | |
| *A61K 35/655* | (2015.01) | |
| *A61K 31/726* | (2006.01) | |
| *A61K 31/737* | (2006.01) | |

(52) U.S. Cl.
CPC ............. *A61K 36/03* (2013.01); *A61K 8/97* (2013.01); *A61K 8/987* (2013.01); *A61K 9/0014* (2013.01); *A61K 31/726* (2013.01); *A61K 31/737* (2013.01); *A61K 35/655* (2015.01); *A61K 47/46* (2013.01); *A61Q 19/00* (2013.01); *A61K 2236/37* (2013.01); *A61K 2800/75* (2013.01)

(58) Field of Classification Search
None
See application file for complete search history.

(56) References Cited

U.S. PATENT DOCUMENTS

| 8,075,928 B2 | 12/2011 | Soma, et al. | |
|---|---|---|---|
| 2007/0172492 A1 | 7/2007 | Soma, et al. | |
| 2010/0093847 A1* | 4/2010 | Kazuo ................. | A61K 31/336 514/475 |
| 2012/0058134 A1 | 3/2012 | Soma | |

FOREIGN PATENT DOCUMENTS

| KR | 1020060064681 | 6/2006 |
|---|---|---|
| KR | 1020070024147 | 3/2007 |
| KR | 1020080085432 | 9/2008 |
| KR | 1020080111787 | 12/2008 |
| KR | 20100025237 A | 3/2010 |

OTHER PUBLICATIONS

Inagawa, et al.; "Homeostasis as Regulated by Activated Macrophage. II. LPS of Plant Origin Other Than Wheat Flour and Their Concomitant Bacteria", Aug. 17, 1991; 4 pages.

Maruyama, et al.; "Suppression of Th2 Immune Responses by Mekabu Fucoidan from Undaria pinnatifida Sporophylls," Sep. 21, 2014; 6 pages.

International Search Report dated Apr. 1, 2013 corresponding to International Patent Application No. PCT/KR2012/009070; 3 pages.

Chinese Office Action dated Jan. 12, 2017 for Chinese application No. 201280073440.9.

Chinese Office Action dated Sep. 1, 2017 for Chinese application No. 201280073440.9.

* cited by examiner

*Primary Examiner* — Chris R Tate
*Assistant Examiner* — Randall Winston
(74) *Attorney, Agent, or Firm* — Ohlandt, Greeley, Ruggiero & Perle, LLP (57) ABSTRACT

The present invention relates to a composition comprising an extract of a mixture of *Undaria pinnatifida* sporophylls and ascidian shells for treating atopic dermatitis, wherein the composition has the excellent effect of treating atopic dermatitis through the synergistic interaction of the anti-inflammatory effect of *Undaria pinnatifida* sporophylls and the cell regenerative effect of ascidian shells. The composition of the invention is not involved in the suppression of cytokine production. However, it is assumed that the composition has the effects of suppressing inflammation as well as regenerating skin.

13 Claims, 5 Drawing Sheets

No-1 BEFORE APPLICATION    No-1 AFTER APPLICATION

FIG. 3

No-2 BEFORE APPLICATION    No-2 AFTER APPLICATION

FIG. 4

No-3 BEFORE APPLICATION          No-3 AFTER APPLICATION

FIG. 5

No-4 BEFORE APPLICATION    No-4 AFTER APPLICATION

COMPOSITION COMPRISING EXTRACT OF MIXTURE OF *UNDARIA PINNATIFIDA* SPOROPHYLLS AND ASCIDIAN SHELLS FOR TREATING ATOPIC DERMATITIS

CROSS-REFERENCE TO RELATED APPLICATIONS

This application claims priority from Korean Patent Application No. 10-2012-0054488, filed on May 22, 2012, in the Korean Intellectual Property Office, the entire disclosures of which is incorporated herein by reference for all purposes.

BACKGROUND

Field

The present inventive concept relates to a composition effective for alleviating atopic dermatitis comprising extract of mixture of *Undaria pinnatifida* Sporophyll and ascidian shell and a method for manufacturing the composition.

Description of the Related Art

Atopic dermatitis not only includes skin inflammation, pigmentation, itching, etc. but also accompanies mental stress due to frequent recurrence which causes increase in time required for the treatment of atopic dermatitis. In addition, misdirected information on the treatment of atopic dermatitis causes distrust of the steroid treatment, and many are searching for secondary treatment or home remedy, which leads to serious inconvenience to patients and increase in cost for the treatment.

To treat atopic dermatitis, as the conventional remedies, substances such as ceramide, linoleic acid, vegetable oil or mineral oil, steroids such as hydrocortisone, formulations which add antibacterial and anti-inflammatory functions to steroids, the DNA synthesis inhibitor via ultraviolet therapy, hyperplastic cell inhibitors, inflammation and pruritus inhibitor have been proposed.

However, the steroid may lead to adverse side effects such as epidermal growth inhibition, and urea peroxide may lead to over-irritation to skin, and antibiotic substance such as antihistamines may lead to side effects such as tolerance of bacteria and photosensitivity disease.

The exact pathogenesis of atopic dermatitis is not yet fully understood, but it has been reported that immunological and non-immunological mechanism is involved along with genetic factors. Extrinsic atopic dermatitis which takes most part of atopic dermatitis is caused by immune mechanism associated with immunoglobulin E (IgE). It has been largely reported that delayed immunological reaction due to abnormal T-cells is more involved in extrinsic atopic dermatitis, rather than immediate immunological reaction toward allergen.

Further, these days, it has been reported that Th2-related cytokines such as interleukin (IL)-4 which generates the production of IgE from B cells causes atopic dermatitis. Therefore, the biggest problem with atopic dermatitis is increase in cytokines by rise in inflammatory reaction due to abnormal activation of the immune function.

In recent studies, it has been reported that, if proteinase-activated receptor-2 (PAR-2) which is protease-activation acceptor present in cell membrane is increased and activated, the mechanism in a cell, IκB kinase (IKK)→nuclear factor kappa B (NF-κB), is activated and increases inflammatory response, and as a result, various inflammatory materials such as cytokines (tumor necrosis factor (TNF)-α, IL-6, IL-10) cyclo-oxygenase (COX)-2, cytokine-inducible nitric oxide synthases (iNOS), adhesion molecules are increased, aggravating atopic dermatitis.

In other words, PAR-2 activation causes inflammation and pigmentation of the skin, itching, etc., and thus, suppression of PAR-2 activation is thought to be helpful in alleviating atopic dermatitis. According to recent studies, the PAR-2 inhibitors which are clinically used as a topical agent alleviate atopic dermatitis, and therefore, it is likely that PAR-2 inhibitors can be developed as a topical medication.

SUMMARY

Exemplary embodiments overcome the above disadvantages and other disadvantages not described above. Also, exemplary embodiments are not required to overcome the disadvantages described above, and an exemplary embodiment may not overcome any of the problems described above.

An exemplary embodiment is purposed to provide a composition effective for alleviating atopic dermatitis containing extract of mixture of *Undaria pinnatifida* Sporophyll extract and purified ascidian shell, and a method for manufacturing the composition.

According to an aspect of an exemplary embodiment, a composition effective for alleviating atopic dermatitis containing extract of mixture of *Undaria pinnatifida* Sporophyll extract and purified ascidian shell is provided.

In an exemplary embodiment, the *Undaria pinnatifida* Sporophyll extract may be hot-water extract, and may contain fucoidan as an active ingredient. Preferably, the extract may be an extract extracted using hot-water with deionized water, but is not limited thereto. If including fucoidan as an active ingredient, the extract may be obtained from various extract method such as alcohol extracting method.

In an exemplary embodiment, the *Undaria pinnatifida* Sporophyll extract may be *Undaria pinnatifida* Sporophyll from Gijang of Busan or Tongyeong or Gyeongnam. In an exemplary embodiment of the present disclosure, the *Undaria pinnatifida* Sporophyll cultivated at Yongcho-do, Hansan-myeon, Tongyeong of Gyeongnam and Gijang of Busan was used.

In an exemplary embodiment, the purified ascidian shell may be ascidian shell dry powder, and may contain glycosaminoglycan as an active ingredient. However, if the extract contains glycosaminoglycan as an active ingredient, the extract may be obtained from various extract method such as alcohol extracting method.

In an exemplary embodiment, a mixing ratio of the *Undaria pinnatifida* Sporophyll extract and the purified ascidian shell may be preferably 1:0.5 to 1:4.

In an exemplary embodiment, the composition effective for alleviating atomic dermatitis may be used for various uses such as food composition, cosmetic composition, or pharmaceutical composition.

According to another exemplary embodiment, a method for manufacturing a composition effective for alleviating atopic dermatitis containing extract of mixture of *Undaria pinnatifida* Sporophyll extract and purified ascidian shell is provided.

1) obtaining powder by drying and crushing *Undaria pinnatifida* Sporophyll and ascidian shell 2) obtaining *Undaria pinnatifida* Sporophyll extract by boiling *Undaria pinnatifida* Sporophyll powder obtained from 1) and using centrifugal;

3) obtaining a mixed extract by mixing, heating, and stirring the *Undaria pinnatifida* Sporophyll extract obtained from 2) and the ascidian shell powder obtained from 1).

In an exemplary embodiment, in the step 1), drying may include natural dry in air for 1-5 days, and then drying in a dryer at temperature of 80-150° C. for 0.5 to 4 hours.

In an exemplary embodiment, in the step 2), water may be deionized water. In an exemplary embodiment, in the step 3), the mixture may be heated at temperature of 40 to 80° C. for 10 to 120 minutes, and then stirred at a speed of 300 to 700 rpm for 0.5 to 3 hours.

Effect of the Invention

Composition effective for alleviating atopic dermatitis according to the present general inventive concept includes extract of mixture of *Undaria pinnatifida* Sporophyll extract containing fucoidan as an active ingredient and purified ascidian shell containing glycosaminoglycan, and thus, synergic effect from the anti-inflammatory effect of *Undaria pinnatifida* Sporophyll extract and cell regeneration effect of purified ascidian shell shows excellent effect to alleviate atomic dermatitis.

The composition of the present general inventive concept does not relate to suppression of generation of cytokines, but it is assumed that the composition has the effect to suppress inflammation and regenerate skin. In addition, the composition is made of natural substances, and thus is non toxic and safe to use for long-term use.

BRIEF DESCRIPTION OF THE DRAWING FIGURES

The above and/or other aspects of the exemplary embodiments will be more apparent with reference to the accompanying drawings, in which.

DETAILED DESCRIPTION OF THE EXEMPLARY EMBODIMENTS

Certain exemplary embodiments will now be described in greater detail with reference to the accompanying drawings.

In the following description, the same drawing reference numerals are used for the same elements even in different drawings. The matters defined in the description, such as detailed construction and elements, are provided to assist in a comprehensive understanding of the exemplary embodiments. Thus, it is apparent that the exemplary embodiments can be carried out without those specifically defined matters. Also, well-known functions or constructions are not described in detail since they would obscure the invention with unnecessary detail.

The term "about" refers to change about 30, 25, 20, 25, 10, 9, 8, 7, 6, 5, 4, 3, 2 or 1% of reference quantity, level, value, number, frequency, percentage, dimension, size, amount, weight or length.

In addition, other components listed above, the term "including", "configuration" or "having", which means not specifically mention the opposite, the components may be inherent, so to exclude but also can include other components that should be interpreted. All terms, including technical and scientific terms that are generally understood by those of ordinary skill in the art, the present invention pertains, unless otherwise defined, shall have the same meaning.

The present invention will now be described in detail.

A Composition for Improving Atopic Dermatitis

The composition effective for alleviating atopic dermatitis according to the present general inventive concept includes extract of mixture of *Undaria pinnatifida* Sporophyll extract and purified ascidian shell.

The *Undaria pinnatifida* Sporophyll is a sporophyll of seaweed belonging to baling of brown algae. The *Undaria pinnatifida* Sporophyll is known to be a functional food having anti-bacterial, anti-cancer functions with high growth potential. There are a lot of recent studies on whitening and anti-oxidation, and thus, a variety of physiological activities would be expected. In particular, it has been reported that there are a lot of studies on whitening of seaweed polysaccharides such as fucoidan, and 3 times higher (6.65%) fucoidan is contained in *Undaria pinnatifida* Sporophyll than kelp (2.71%).

Further, in the present inventors' recent study, it has been revealed that ascidian skin contains glycosaminoglycan as the active ingredient, and ascidian tunic extract has no irritation to skin, excellent effect such as suppression of activation of collagenase, activation of collagen production, and good cell regeneration activity, which are related to reducing wrinkle, that it is helpful for anti-wrinkle care (Korean Patent application No. 10-2012-0045314).

Thus, the present inventors have examined in vitro and in vivo physiological activity of a mixture of fucoidan of *Undaria pinnatifida* Sporophyll having immune-enhancing, anti-bacterial, anti-cancer effects and glycosaminoglycans of ascidian shell and simultaneously evaluated change in condition of skin when these substances are applied to a patient with atomic dermatitis.

As a result, *Undaria pinnatifida* Sporophyll extract and purified ascidian shell are not involved in suppression of generation of cytokine, but *Undaria pinnatifida* Sporophyll extract has the anti-inflammatory effect, and GAG of ascidian shell has cell regeneration effect. In this regard, it appears that the composition of the present general inventive concept has outstanding anti-inflammatory effect and skin regeneration effect rather than suppressing cytokine.

In addition, the inventors of the present invention found the optimal mixture ratio of *Undaria pinnatifida* Sporophyll extract and purified ascidian shell. The ratio may be from 1:0.5 to 1:4, preferably 1:1 to 1:2, particularly preferably about 1:1. In case when the ratio of *Undaria pinnatifida* Sporophyll extract to purified ascidian shell is less than 0.5, the anti-inflammatory effect and skin regeneration effect would be low, and if the ratio exceeds 4, it has the similar effect when the ratio is not more than 4, and thus, there is no reason to raise the portion of purified ascidian shell.

Further, the composition may be used for food compositions, cosmetic compositions, or pharmaceutical compositions, and has no limitation in a range of use.

The pharmaceutical composition may be prepared by including a pharmaceutically acceptable vehicle, diluent, excipient, or a combination thereof.

The vehicle is defined as a compound which easily adds compounds into cells or tissues. The pharmaceutically acceptable vehicles include, for example, ion exchange resin, alumina, aluminum stearate, lecithin, serum proteins (e.g., human serum albumin), buffer substances (e.g., various phosphates, glycine, sorbic acid, potassium sole Bate, partial glycerides of saturated vegetable fatty acid mixture), water, salts or electrolytes (e.g., protamine sulfate, disodium hydrogen phosphate, potassium monohydregen phosphate, sodium chloride, and zinc salts), colloid silica, magnesium trisilicate, polyvinylpyrrolidone, cellulose-based substrate, a polyethylene glycol, sodium carboxymethylcellulose, polyarylate, waxes, polyethylene glycol, and the like, but is not limited thereto.

Further, the vehicle must be compatible with the active ingredient of the present general inventive concept. The vehicle may mix at least one of saline, sterile water, Ringer's solution, buffered saline, dextrose solution, maltodextrin solution, glycerol, ethanol, and if necessary, the vehicle may add conventional additives such as antioxidants, buffers, and fungistats.

Wherein the diluent is defined as a compound which is diluted in water, and stabilizes the biologically active form of the compound. Salts dissolved in buffered solutions are utilized as diluents in the art. A commonly used buffer solution is phosphate-buffered saline, which mimics salt condition of the human. The buffer salt may control the pH of the solution at low concentration, and it is rare that the buffer diluents deforms biological activity of compounds.

The excipients include, for example, starch, calcium carbonate, sucrose, lactose and gelatin for solid preparations, wetting agents, sweeteners, aromatics and preservatives, etc.

If necessary, the pharmaceutical composition is a pharmaceutically acceptable component, which may further include at least one of wetting agents, buffering agents, suspending agents, lubricants, emulsifying agents, disintegrants, absorbents, preservatives, surfactants, colorants, flavorants, sweeteners, and additional therapeutic agents.

In addition, pharmaceutical compositions of the present general inventive concept is delivered to a subject via oral, transdermal, intravenous, topical, inhalation, or rectal methods, and the delivery may be by sustained release. The pharmaceutical compositions may be administered by method selected from a group consisting of capsules, tablets, powders, granules, syrups, injectable fluids, creams, ointments, hydrophilic ointments, inhalable fluids, and suppository.

A pharmaceutical composition according to the present invention may be administered by any means known to those skilled in the art. For example, the compound in the present invention may be administered through oral, non-oral, inhalation spray, topical, rectal, nasal, buccal, vaginal means, or implanted reservoir. Here, the term "non-oral" refers to the subcutaneous, intraperitoneal, intrathecal, oral tablets, intravenous, intramuscular, intra-arterial, intramedullary, intrathecal, within the heart, transdermal, subcutaneous, intraperitoneal, intestinal, sublingual and infusion techniques. Exact administration protocol is changeable depending on various elements such as the patient's age, body weight, general health condition, gender, and diet; determination of specific administration procedures are obvious to one of ordinary skill in the art.

The pharmaceutical compositions of the present invention may be administered by one single dose, multiple discrete doses, or continuous infusion. Pump means, particularly subcutaneous pump means is useful for continuous infusion.

A dosage unit of the pharmaceutical composition according to the present invention may include, for example, the individual dosages of 1, 2, 3 or 4 times, or ½, ⅓ or ¼ times. The individual dose includes the amount that active ingredient is administered once, which usually equals to ½, ⅓ or ¼ times the daily dose. Effective amount of extract of mixture of *Undaria pinnatifida* Sporophyll extract and purified ascidian shell are concentration-dependent, but preferably the amount is 0.1 mg to 1,000 mg/kg, and more preferably from 0.1 to 500 mg/kg, and can be administered for 1-6 times a day. Thus, the pharmaceutical composition may be administered to the body by 0.1~6,000 mg/day per 1 kg of body weight of an adult.

The dose levels may change depending on various factors including particular activity and the possible toxicity of a particular compound; patient's age, body weight, general health, gender and diet; administration time; discharge rates; the drug combination; severity of the disease; administration type.

Typically, the in vitro capacity-effect results provide a useful guideline for suitable dosage for a patient. Furthermore, this result is useful for studies in animal models. In order to determine the appropriate dose level, the matters to consider are well known in this field, and belong to an ordinary skill of a general doctor.

Any known dosage therapy based on regular time and for continuation of the drug delivery may be considered required for effective treatment and may be re-experienced. The therapy may include pre-treatment and/or combined administration with additional therapeutic agent (s).

Dosage of the pharmaceutical compositions of the present disclosure is vary in range depending on a patient's body weight, age, gender, health condition, diet, administration time, administration method, excretion and severity of the disease, and a normal expert in the art of may determine the dosage easily.

The food composition is preferably health and functional food composition which may indicate anti-inflammatory activity by extract of mixture of *Undaria pinnatifida* Sporophyll extract and purified ascidian shell. As used herein, "health functional food" means general foods by adding an extract of the present invention to general foods for improving functionality of food, and the food may be manufactured by adding the extract to general foods, by being encapsulated or powdered, or as suspension. If ingested, it can cause specific effects to health, and it has no side effect for long-term dose, as food is a raw material, unlike general drugs.

When the extract of the present invention is used as a food additive, the extract may be added as it is, or may be used along with other foods or other food components indicating therapeutic activity for atomic dermatitis. Other conventional methods may be used, as appropriate. The amount of the active ingredient may be determined appropriately depending on the purpose of use (prevention, health or therapeutic treatment). Generally, when manufacturing a food or beverage, a raw material based on the total weight of 0.0001 to 30% by weight, preferably 0.0001 to 10% by weight, more preferably in an amount of 0.1 to 5% by weight may be added. However, for the purpose of health and hygiene or for the purpose of health control, in the case of long-term intake, the amount may be adjusted to be below the above range. In addition, in the case of long-term intake for health control, the amount may be changed to below the above range. Further, it is preferable that the health food of the present invention contains extracts within the measured toxicity, in case of using the pharmaceutical composition.

There is no particular restriction on the type of food, such as meat, sausage, bread, chocolates, candies, snacks, cookies, pizza, noodles and other noodles, gums, milk powder, cooked food, uncooked food, fermented milk, dairy products including ice cream, various soups, beverages, tea, drinks, alcoholic drinks and vitamin complex, and so on. For example, a certain concentration of anthocyanin-polysaccharide complexes of the present invention may be used for drinks or foods such as milk or yogurt.

The food composition of the present invention may include, in addition to the active ingredients, various flavors or natural carbohydrates as additional ingredients, and aside from the foregoing, may contain various nutrients, vitamins, electrolytes, flavoring agents, coloring agents, pectic acid and its salts, alginic acid and salts thereof, organic acid, protective colloidal thickeners, pH adjusting agents, stabilizers, preservatives, glycerin, alcohol, carbonated agent used in carbonated drinks and the like. These additive components may be added for the amount from 0.0001 to 10 parts by weight of the composition.

In the cosmetics chemical composition of the present invention, the extract of the present invention may be added as it is, may be used along with other cosmetic ingredients, or may be used appropriately according to a conventional method. In general, the amount of the active ingredient mixture may be determined suitably depending on the purpose of use thereof. In general, the extract of the present invention may be added by the total weight of 0.0001 to 10% by weight, preferably in an amount of 0.1 to 5% by weight for the entire weight of raw material when manufacturing cosmetics. For cosmetics, the extract may be used for toner, lotion, cream, packs, and color cosmetics, etc., but is not limited thereto.

A Method for Manufacturing of *Undaria pinnatifida* Sporophyll Extract and Ascidian Shell Extract Extract of mixture of *Undaria pinnatifida* Sporophyll extract and ascidian shell dry powder which is effective for alleviating atomic dermatitis according to the present invention may be manufactured by the processes as shown below:

1) *Undaria pinnatifida* Sporophyll and ascidian shell are dried and crushed to obtain powder;

2) The *Undaria pinnatifida* Sporophyll powder obtained from above 1) is put to water and heat in boiling water, and is centrifuged to obtain *Undaria pinnatifida* Sporophyll extract; and 3) By heating and stirring the *Undaria pinnatifida* Sporophyll extract obtained from the above 2) and ascidian shell powder obtained from the above 1), obtain mixture extract.

In step 1), the *Undaria pinnatifida* Sporophyll and ascidian shell may be naturally obtained or cultured, may be obtained from domestic or foreign, and is not particularly limited. The drying is performed for 1 to 5 days using natural drying in air, and then, they may be dried at 80 to 150° C. temperature for 0.5 to 4 hours in a dryer.

Wherein in step 2) water as a solvent, specifically, purified water or deionized water in an amount of 4 to 15 times of *Undaria pinnatifida* Sporophyll is boiled in water at using 90 to 150° C. Then cooled, and the precipitate is removed via centrifugation, and then *Undaria pinnatifida* Sporophyll extract is obtained.

In step 3), *Undaria pinnatifida* Sporophyll extract and ascidian shell powder are heated at 40 to 80° C. for 10 to 120 minutes and then stirred at a rate of 300 to 700 rpm for 0.5 to 3 hours to obtain a mixture extract. At this time, the mixing ratio between *Undaria pinnatifida* Sporophyll extract and ascidian shell powder is preferably from 0.5:1 to 4:1.

As mentioned above, in an extract of mixture of *Undaria pinnatifida* Sporophyll extract and ascidian shell dry powder, fucoidan ingredients in *Undaria pinnatifida* Sporophyll has the anti-inflammatory effect, glycosaminoglycans in the ascidian shell extract ingredients has collagenase inhibitory activities, and promote collagen production and cell regeneration activity.

Accordingly, the mixed extract containing the composition of the present invention is useful for alleviating and treating atopic dermatitist.

Hereinafter, the present invention will be described in further detail with reference to the examples shown below. However, the following examples are to illustrate the invention only and the present invention is not limited thereto.

Example 1

1-1. Step of Manufacturing *Undaria pinnatifida* Sporophyll Powder and Ascidian Shell Powder The *Undaria pinnatifida* Sporophyll used in this experiment is from Gyeongnam Tongyeong Hansanmyeon Yongchodo (A-1) and Busan Gijang (A-2). In addition, the ascidian shell is collected from Suryuk Town of Tongyeong, and went through the washing process. After air-dry for three days and then they were dried in a dryer at 1.07° C., for 2 hours. After drying, *Undaria pinnatifida* Sporophyll powder and ascidian shell powder were obtained as a sample in the process of the first and second crushing processes.

Figure 1:
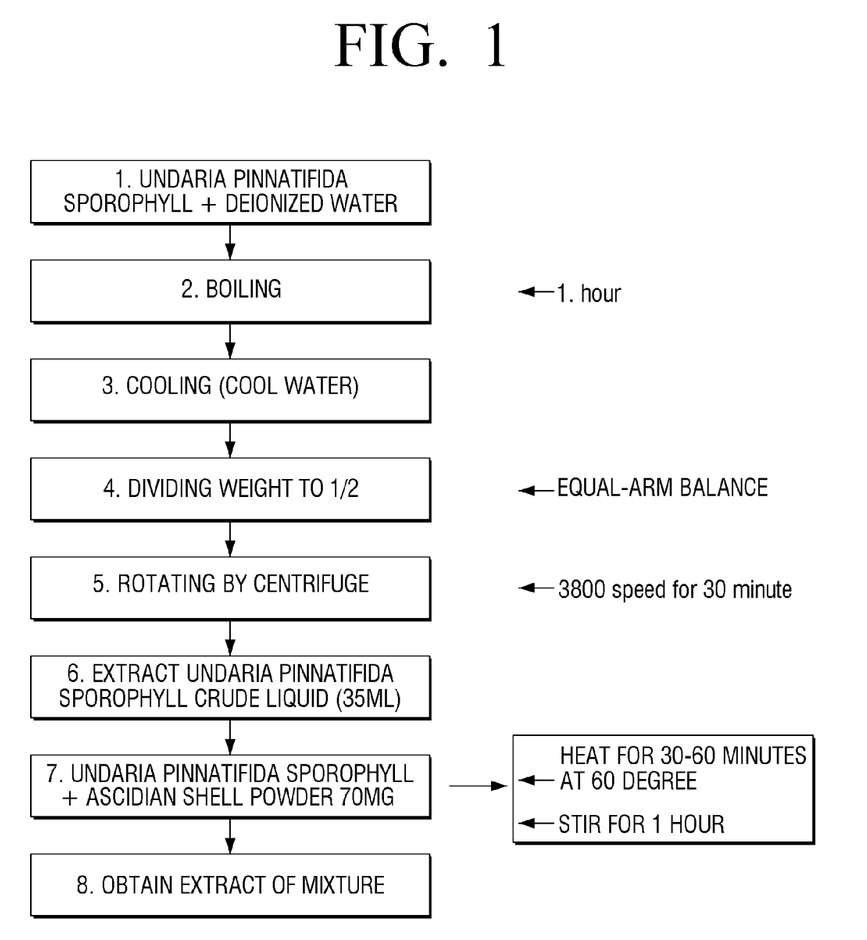
FIG. 1 is a flowchart of a manufacturing process of a composition extract according to an exemplary embodiment.

1-2. Step of Obtaining Extract of Mixed Powder of *Undaria pinnatifida* Sporophyll and Ascidian Shell As shown in the flowchart of FIG. 1, *Undaria pinnatifida* Sporophyll powder sample 30 g is mixed well with 180 ml of deionized water for 1 hour, is boiled in water for 1 hour, and then is cooled in cold water. After weighing at two-armed scale, the above is divided in half, and then is rotated for 30 minutes at a centrifuge with 3,800 speed. After obtaining extract by 35 ml, it is measured by a salinity meter with 56% and Bix 7.

After measuring *Undaria pinnatifida* Sporophyll extract 35 ml and ascidian shell powder 70 mg, heat the sample for 30 to 60 minutes at 60° C. Then, at a speed of 500 rpm, it is stirred for one hour to obtain the extract of mixture.

<Experimental Example 1> Clinical Effects for Atopic Dermatitis

Figure 2:
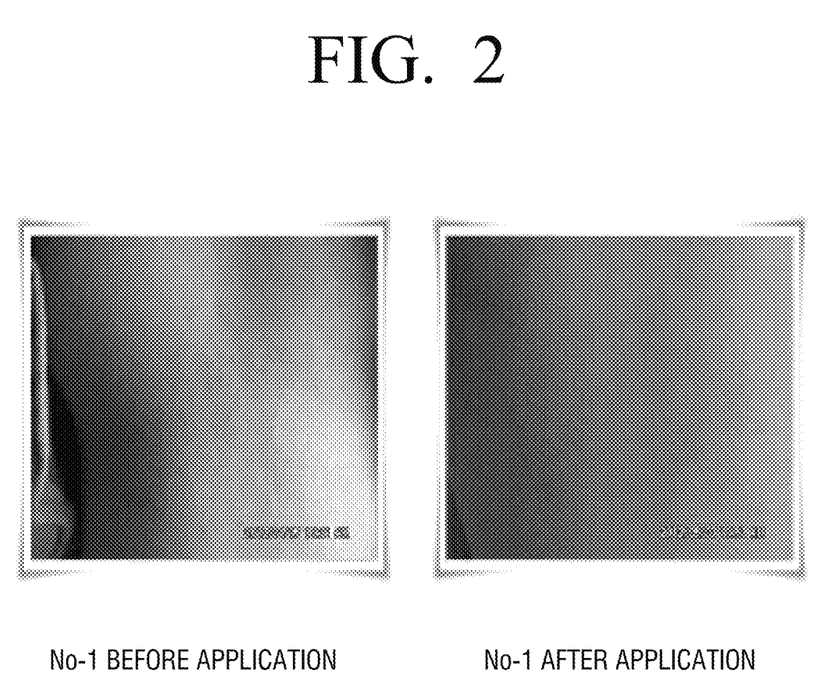
FIGS. 2-5 are photos comparing before treatment and after treatment of atopic dermatitis according to experimental example 1.
Figure 3:
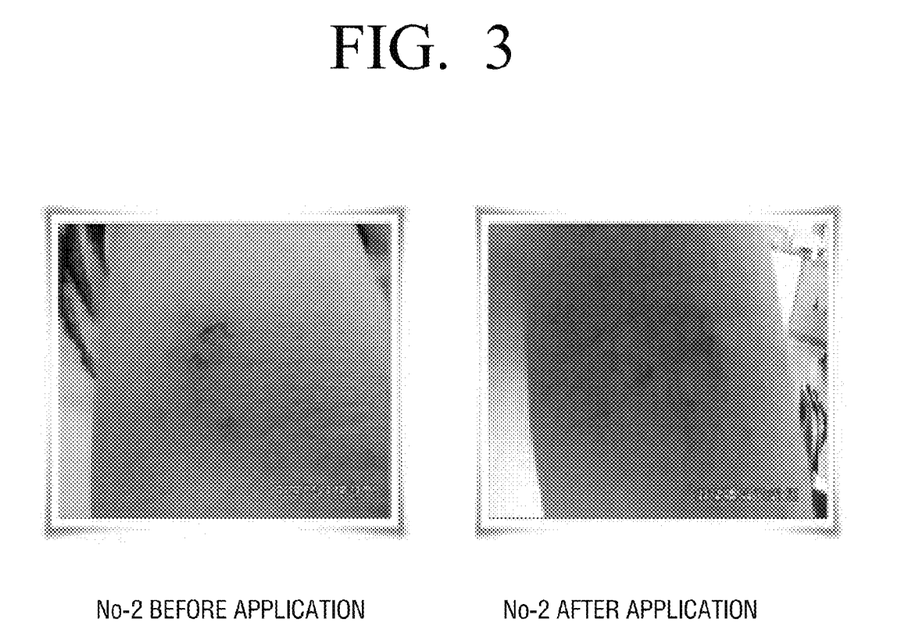
Figure 4:
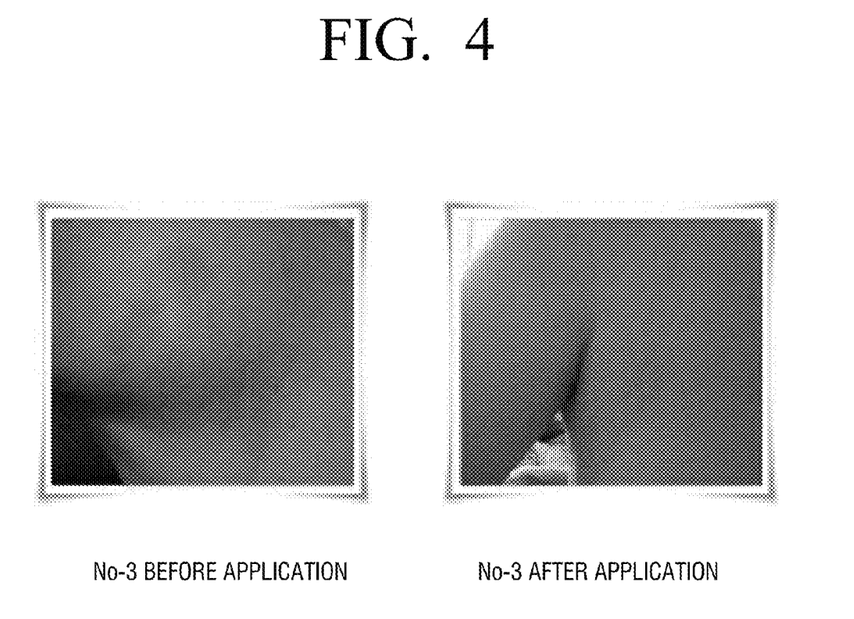
Figure 5:
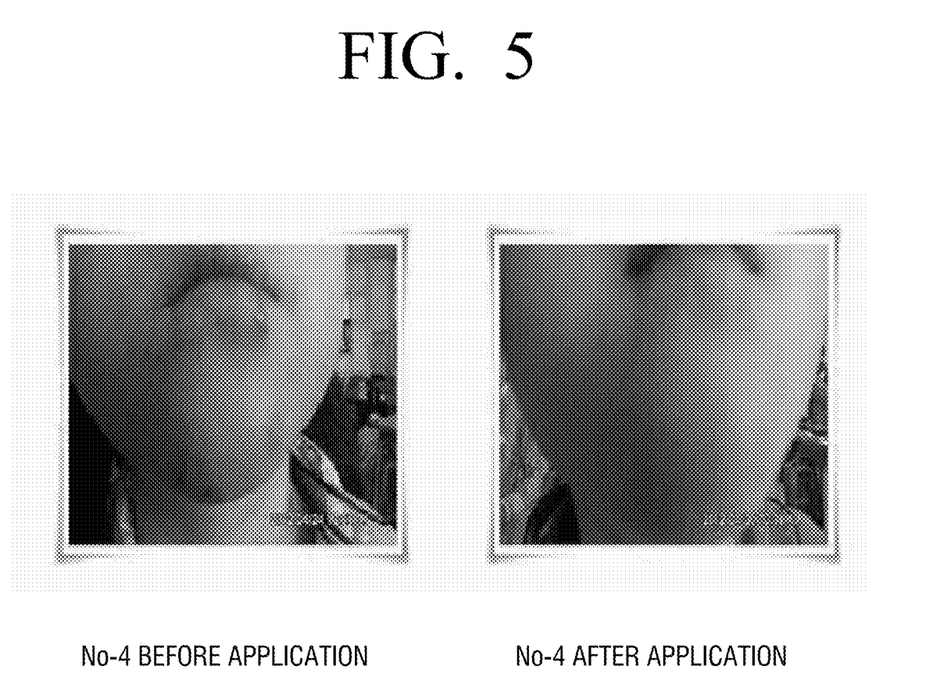

In this study, a clinical test was conducted for 20 subjects who were suffering from atopic dermatitis. After integrating 4-week clinical test results, atopic dermatitis' condition of the subjects, and the researcher's observation, changes in the skin of atopic dermatitis is summarized and tabled as shown in Table 3. FIGS. 2-4 are photos comparing results after use of extract of mixture of *Undaria pinnatifida* Sporophyll and ascidian shell powder for 2 weeks.

In accordance with the observation of the researcher, and self-observed change in atopic dermatitis of the subjects, the extract of mixture has positive efficacy to the subjects of various ages and various forms of diseases. Among the subjects, a 53-year-old man, after 3 days, experienced that itchiness has been decreased, red spots have been reduced, and only slight scars were left. After three weeks, the man was almost cured. Itchiness of 16 subjects who spent a week in clinical test is significantly reduced from 1 week after beginning use of the extract, 1 subject after 2 weeks, and 1 subject after 3 weeks experienced reduction of symptoms. Symptoms of seven of the entire subjects were almost alleviated after 4 weeks.

The results show that the mixed extract of *Undaria pinnatifida* Sporophyll and ascidine tunic has significantly contributed to alleviate atopic dermatitis. Looking the process in which the subjects' atopic dermatitis has been alleviated, even though the same extract of mixture was used, the process of treatment was different by subjects.

Therefore, it is known that many different factors of subjects such as their personal characteristics and physical constitutions affect the results.

TABLE 1

Questionnaire of Atopic dermatitis

| No | Gender | Age | Before | After 4 weeks |
|---|---|---|---|---|
| 1 | F | 8 | Lots of red spots over the entire face, severe itching | Itching almost disappeared, and red sots cleanly removed |
| 2 | M | 8 | Itchy face(upper eyes, around forehead, mouth, nose) and body | Symptoms were alleviated while applying the extract but occurred again |
| 3 | F | 8 | Slight itching | Itching has removed and skin became cleaner |
| 4 | F | 8 | Festered and itchy lips | When applying the extract to festered skin, scar is recovered and scab is generated. Itching is reduced. |
| 5 | M | 10 | Somewhat severe, but gradually recovered by taking his medicine | When a lot amount of the extract is applied, 1-2 protruding things were found, but in case of small application, the effect is not significant. |
| 6 | F | 11 | Slight itching, skin discoloration | Effect of soothing itching |
| 7 | F | 11 | Severe itching | Soothing reduced, red spots lightened |
| 8 | M | 11 | Sometimes itchy at arm folds | Itching reduced, scar healed |
| 9 | F | 11 | Arm folds are still itchy | For first application, itching was continued, but continued application reduced itching |
| 10 | F | 12 | Severe scratch marks around elbows, legs, and skin discoloration | Skin color became bright and clean. |
| 11 | F | 12 | Scab on lips, red spots and severe itching at elbows, leg folds, and back | Scab on lips became smaller, itching was alleviated. |
| 12 | F | 13 | Dry skin, slight itching | When applying for itchy skin, red part disappeared. |
| 13 | F | 13 | Slight itching | Itching was reduced, when the extract applied |
| 14 | M | 19 | Mild symptom | Not much improvement until 1 week |
| 15 | F | 21 | Peeled skin, itchy, red, and swollen skin | Alleviated itching |
| 16 | M | 21 | Dry and itchy | Treatment agent is very sticky, but itching was alleviated a lot, red skin were reduced. |
| 17 | F | 24 | Face is itchy and red | After 2 weeks, itching was reduced, and after 4 weeks, red skin was alleviated |
| 18 | M | 50 | Dry skin, severe itching on back | After 1 week, itching was disappeared when the extract is applied. |
| 19 | M | 53 | Red spots around back and armpit and dry skin | After 3 days, itching was disappeared, and red spots were removed. |
| 20 | F | 74 | Severe itching, scars at arms and furuncle scab on skin | Size of furuncle scab decreased, and itching was reduced |

<Experimental Example 2> Mixed Extract Purification Experiments; Measurement of the Anti-Inflammatory Effect (1) Cytotoxicity Measurement All the cell lines used in the experiment was received from the Korea Cell Line Bank (KCLB, Seoul, Korea). Each cell line was cultured in 10 cm well plate, and subcultured 2-3 times a week, and as to the medium, 10% FBS medium was used as the growth medium. Cell lines were cultured in an incubator which is controlled to have humidity 95%, 5% $CO_2$, 36.5° C., and the medium was exchanged once every two days.

Cytotoxicity of fucoidan extracts was determined with RAW264.7 cell. That is, RAW264.7 cells cultured in a flask for cell culturing were cultured with the medium of Dulbecco's Modified Eagle's Medium (DMEM) containing 10% of FBS. With the concentration of $1\times10^4$ cells/well, the cells were divided in % well plate, and cultured at a $CO_2$ incubator controlled to have 35° C., humidity 95%, $CO_2$ 5% for 24 hours. Samples were dissolved in a fresh medium so that final concentration thereof becomes 0.1, 1, 10, 100 and 200 μg/mL, and then the cell lines were treated with the dissolved samples and incubated for 24 hours. In order to measure survivable of cell lines, the absorbance is measured at 490 nm using MTS reagent via microplate reader (Molecular Devices, VersaMax ELISA Microplate Reader, USA). Survival rate of the cells was indicated as the absorbance of the sample-treated group against the absorbance of control group which is not sample-treated.

GAG of ascidine shell and *Undaria pinnatifida* Sporophyll extract 0.1, 1, 10, 100 and 200 μg/mL were added to the RAW 264.7 cell line, and toxicity on the cells was measured. As a result of the measurement, cell toxicity was not observed in the above-said concentration range.

TABLE 2

Cell toxicity of RAW264.7 cell line after 24-hour sample treatment

| | Sample concentration (μg/mL) | Cell survival (%) |
|---|---|---|
| Control | | 100.0 ± 4.0 |
| GAG | 0.1 | 102.3 ± 2.8 |
| | 1 | 101.2 ± 4.4 |
| | 10 | 107.1 ± 2.9 |
| | 100 | 109.3 ± 2.7 |
| | 200 | 100.2 ± 2.3 |
| GAG:TSM (1:1) | 0.1 | 96.6 ± 2.8 |
| | 1 | 99.4 ± 2.5 |
| | 10 | 105.4 ± 2.5 |
| | 100 | 104.0 ± 2.0 |
| | 200 | 102.3 ± 3.5 |
| TF | 0.1 | 99.9 ± 4.5 |
| | 1 | 91.7 ± 8.4 |
| | 10 | 107.7 ± 1.5 |
| | 100 | 109.5 ± 2.4 |
| | 200 | 109.2 ± 4.4 |
| GF | 0.1 | 102.6 ± 3.4 |
| | 1 | 107.1 ± 4.4 |
| | 10 | 104.6 ± 2.4 |
| | 100 | 110.2 ± 2.5 |
| | 200 | 109.5 ± 2.5 |

GAG: Glycosaminoglycans,
TSM: Tongyeong *Undaria pinnatifida* Sporophyll extract,
TF: Tongyeong *Undaria pinnatifida* Sporophyll fucoidan,
GF: Gijang *Undaria pinnatifida* Sporophyll fucoidan.

(2) Measurement of the Generation Amount of Nitric Oxide (NO)

After subculturing RAW264.7 cell lines to the 96 well, they were incubated until the cells cover about 70 to 80% of the floor. As a control group, untreated sample group was used and as a positive control group, lipopolysaccharide (LPS) was treated with the concentration of 1 μg/mL. The test group is treated to be the final sample concentration of 0.01, 0.1, 1, 10, 100, and 200 μg/mL with the same LPS concentration as the positive control group, and the test group was incubated for 24 hours after treatment. NO generation amount was measured by the Griess reagent. Griess reagent was prepared by adding 1% sulfanilamide to a 5% nitric acid, mixed with 0.1% naphthylethylene diamine dihydrochloride. 50 µl of the supernatant of the cells cultured was taken at a 96 well plate and added with 50 µl Griess reagent. After reacting at room temperature for 15 minutes, absorbance was measured at 540 nm using the reaction microplate reader (Molecular Devices, VersaMax ELISA Microplate Reader, USA). Change in NO generation amount of the sample was indicated the NO generation amount of the sample group against the NO generation amount of the control group for which sample treatment is not conducted.

Nitric oxide (NO) is known to be a substance which is secreted from cells activated by stimulus such as LPS and mediates various immune responses in body. The anti-inflammatory efficacy of ascidian shell GAG and *Undaria pinnatifida* Sporophyll extract was measured by inducing inflammation by treating cell line samples with lipopolysaccharide (LPS), measuring change in the generation amount with RAW264.7 cell line. Each sample was treated with the extract by concentration of 0.1, 1, 10, 100 and 200 µg/mL and compared with the control group (Table 2). LPS is a substance which induces NO generation and inflammatory cytokines generation, and is used as an inflammation inducer.

When compared with NO generation amount of control groups which were not treated with LPS and samples, the extracts obtained from *Undaria pinnatifida* Sporophyll from Tongyeong (TSM) and Gijang (GMS) were found to have NO generation inhibition effect of 61.3% and 68.0% respectively at the concentration of 200 µg/mL. In addition, in 200 µg/mL group where GAG of ascidian shell and *Undaria pinnatifida* Sporophyll boiled water (TSM) were mixed by 1:1, the anti-inflammatory efficacy was confirmed.

However, in case of GAG which was extracted and refined from ascidian shell, TF (fucoidan extract from *Undaria pinnatifida* Sporophyll of Tongyeong), and GF (fucoidan extract obtained from *Undaria pinnatifida* Sporophyll of Gijang), the NO generation inhibition effect which is similar to LPS 1 µg/mL was indicated. In general, NO generation plays a role to kill bacteria or inhibit tumor, but excessive generation may cause damage to organs, transformation of genetics, and damage to nerves.

(3) Measurement of PGE2 Generation Amount

PGE2 was measured by purchasing the Prostaglandin E2 EIA Kit from Cayman Chemical Company (Ann Arbor, Mich., USA), and the measurement method was quantified according to the manufacturer's analysis method. That is, RAW264.7 cells were pre-treated with 0.1% LPS and seaweed extracts at 1, 10, 100, 200 µg/mL concentration for 24 hours, and then cell culture supernatants was used for measurement of PGE2. The cultured medium was loaded by 50 µL in % well plate coated with goat anti-mouse. Here, primary antibody solution 50 µL and PGE2 conjugate 50 µL were added and reacted for 18 hours at 4° C., and then were washed for five times with a washing buffer. After treating with Ellman's reagent by 200 µL and stirring it for 60~90 minutes, the absorbance was measured at 405~420 nm.

PGE2 which is generated by Cyclooxygenase (COX)-2 is a cause of the symptoms such as erythema, edema, and pain accompanied by inflammatory reaction. In addition, PGE2 has an effect to cell division or proliferation in various biological activities such as inflammatory diseases, and is involved in cause and progression of various diseases. Thus, in order to evaluate which effect the standard fucoidan and *Undaria pinnatifida* Sporophyll fucoidan extract may have on generation of PGE2, the effect of PGE2 generation inhabitation at RAW264.7 cells induced by LPS was measured (Table 4). As a result, it is found that standard fucoidan which is used as the control group inhibits PGE2 generation according to increase in concentration by 71.7% and 38.0% respectively at the concentration of 10, 100 µg/mL GSM and TSM which are samples from *Undaria pinnatifida* Sporophyll boiled water indicated that generation inhibition effect was low at the concentration of 1 µg/mL, but indicated 77.9%, 77.9% and 49.1%, 56.9% at concentrations of 100 µg/mL and 200 µg/mL, showing concentration-dependent PGE2 generation inhabitation. Meanwhile, excessive amount of NO generated in the cell intensifies inflammatory response by facilitating COX-2 activity and inducing synthesis of PG.

TABLE 3

NO production amount of RAW264.7 cell lines after treating with samples

| Sample concentration (µg/mL) | | | NO production (%) |
|---|---|---|---|
| Control + LPS (1 µg/mL) | | | 100.0 ± 3.5 |
| GAG | +LPS | 0.1 | 103.0 ± 4.8 |
| | (1 µg/mL) | 1 | 106.7 ± 4.6 |
| | | 10 | 106.6 ± 2.6 |
| | | 100 | 108.7 ± 4.8 |
| | | 200 | 99.9 ± 8.7 |
| GAG:TSM (1:1) | | 0.1 | 119.6 ± 3.0 |
| | | 1 | 122.3 ± 1.8 |
| | | 10 | 122.9 ± 0.9 |
| | | 100 | 96.2 ± 3.5 |
| | | 200 | 76.5 ± 4.8 |
| TF | | 0.1 | 118.1 ± 1.6 |
| | | 1 | 116.1 ± 1.7 |
| | | 10 | 104.3 ± 8.0 |
| | | 100 | 102.0 ± 3.7 |
| | | 200 | 135.3 ± 1.3 |
| GF | | 0.1 | 120.9 ± 1.9 |
| | | 1 | 118.4 ± 2.8 |
| | | 10 | 120.9 ± 2.1 |
| | | 100 | 116.0 ± 0.5 |
| | | 200 | 189.1 ± 9.5 |
| GSM | | 0.1 | 119.7 ± 6.0 |
| | | 1 | 116.0 ± 3.7 |
| | | 10 | 118.6 ± 3.1 |
| | | 100 | 107.1 ± 1.4 |
| | | 200 | 68.0 ± 3.1 |
| TSM | | 0.1 | 116.4 ± 5.5 |
| | | 1 | 113.5 ± 2.6 |
| | | 10 | 112.3 ± 6.1 |
| | | 100 | 92.0 ± 5.8 |
| | | 200 | 61.3 ± 6.2 |

LPS: lipid polysaccharide,
GAG: glycosaminoglycans,
TF: Tongyeong *Undaria pinnatifida* Sporophyll Fucoidan,
GF: Gijang *Undaria pinnatifida* Sporophyll Fucoidan,
GSM: Gijang *Undaria pinnatifida* Sporophyll Extract,
TSM: Tongyeong *Undaria pinnatifida* Sporophyll Extract

TABLE 4

Inhibition activity of PGE2 by fucoidan and the extract at RAW264.7 cell

| Sample concentration (µg/mL) | | | PGE2 production (%) |
|---|---|---|---|
| Control + LPS (1 µg/mL) | | | 100.0 ± 9.2 |
| Fucoidan | +LPS (1 µg/mL) | 10 | 71.7 ± 11.1 |
| | | 100 | 38.0 ± 10.4 |
| GSM | +LPS (1 µg/mL) | 1 | 93.6 ± 15.4 |
| | | 10 | 98.5 ± 6.3 |
| | | 100 | 77.9 ± 14.6 |
| | | 200 | 49.1 ± 13.3 |

TABLE 4-continued

Inhibition activity of PGE2 by fucoidan
and the extract at RAW264.7 cell

| Sample concentration (μg/mL) | | PGE2 production (%) |
|---|---|---|
| TSM | 1 | 90.1 ± 9.4 |
| | 10 | 97.9 ± 15.7 |
| | 100 | 77.9 ± 5.7 |
| | 200 | 56.9 ± 7.9 |

LPS: lipid polysaccharide
GSM: Gijang *Undaria pinnatifida* Sporophyll Extract,
TSM: Tongyeong *Undaria pinnatifida* Sporophyll Extract <Experimental Example 3> Experiment for Treating Atopic Dermatitis (1) HaCaT Cell Culture and Sample Extraction Cell proliferation was confirmed by HaCaT which is the human skin cell line. That is, HaCaT cell lines which were cultured at a cell culture flask were separated from flask with 1.0 m pipette and subcultured, and cells were cultured with DMEM medium containing 10% FBS. HaCaT cell lines were divided into 96 well plate with the concentration of 1×104 cells/well, and cultivated at a CO2 incubator which was controlled to be 35° C., humidity 95%, CO2 5% for 24 hours. By dissolving the samples in a fresh medium so that final concentration thereof reaches 1, 10, 100, and 200 μg/mL, and then the cell lines were cultivated for 24 hours after treatment. To measure the survival of the cell line, using the MTS reagent, the absorbance at 490 nm was measured by microplate reader (Molecular Devices, VersaMax ELISA Microplate Reader, USA). Survival rate of the cells was indicated as the absorbance of the sample-treated group against the absorbance of the control group for which sample treatment was not conducted.

HaCaT cell, which is Keratinocyte cell line, is cultivated at the DMEM medium containing 10% FBS, and divided in the 12 well plate in 500 μL aliquots, and then the cells were cultivated until the cells cover approximately 70-80% of the floor. Samples in fresh medium were dissolved to reach a final concentration of 0.1, 1, 10, 100 and 200 μg/mL, and after 8-hour cultivation, the medium were changed to KRB (Krebs-Ringer bicarbonate) buffer (115 mM NaCl, 4.7 mM KCl, 1.2 mM MgSO4, 1.28 mM CaCl2, 1.2 mM KH2PO4, 25 mM HEPES, 8.4% NaHCO3 (wt/vol), 1 mg/mL BSA, pH 7.2). After two-hour extraction, KRB solution is collected from each well, and concentration of TNF-α (eBioscience, San Diego, Calif. USA) which is inflammatory cytokines within collected KRB solution and IL-6 was measured using ELISA Kit.

(2) Measurement of the Inflammatory Cytokines Production Amount

TNF-α, IL-6 production amount was measured by using the ELISA kit (eBioscience, San Diego, Calif., USA). After sub-culturing capture antibody to each well by 100 μL and then remaining it at 4° C. for overnight, and then adding Assay diluent by 200 μL. After reacting for 1 hour at room temperature, extract from HaCaT, KRB solution and standard solution of 100 μL were added and reacted for 2 hours at room temperature. After that, detection antibody 100 μL is added to each well, and reacted for 1 hour at room temperature, and then Avidin-HRR 100 uμL was added and reacted for 30 minutes at room temperature. At each preceding step, the sample was washed for 5 times using wash buffer (1×PBS, 0.05% Tween 20/DIW), and was covered for reaction at a dark place. Finally, the substrate solution was added by 100 μL and reacted for 15 minutes, and then stop solution (2 N H2SO4) by 50 μL was treated. The absorbance at 450 and 570 nm was measured using the microplate reader (Molecular Devices, VersaMax ELISA Microplate Reader, USA).

(3) Measurement Results

In order to find out efficacy of fucoidan and the extract for alleviating allergy and examine generation amount of TNF-α and IL-6 which are allergen cytokine, the HaCaT cell line at a final concentration of 0.1, 1, 10, 100 and 200 μg/mL was measured for the effect of inhibition as shown in Tables 5 and 6. In case of fucoidan which was used as a control group, at concentration of 0.1, 1.0 μg/mL, TNF-α generation amount was inhibited by 50.1% and 42.3% respectively, and at concentration of 10 μg/mL or more, the production amount of TNF-α did not change. In contrast, in case of the extract, according to increase in concentrations of samples such as ascidian shell GAG and *Undaria pinnatifida* Sporophyll boiled water, etc., TNF-α generation amount was increased. As a result of measuring IL-6 generation inhibition effect, in case of fucoidan which was used as a control group, when concentration increased, IL-6 generation amount was reduced gradually, and it showed 28.3% inhibition at the concentration of 100 μg/mL. In case of ascidian GMG and *Undaria pinnatifida* Sporophyll, IL-6 production amount increased drastically, in proportion to rise in concentration. In particular, in the case of ascidian shell GAG, TNF-α and IL-6 generation amount increased about 2.4 to 4.3 times.

However, when comparing with the experimental results for patients with allergy, in case of the patient who had red spots over the face, severe itching symptoms, after using GAG:TSM (1:1), the patient's itchiness and red spots completely disappeared. This experiment shows contradictory results compared with cell experiment. This implies that, though *Undaria pinnatifida* Sporophyll extract and purified ascidian shell are not involved in inhibiting the production of cytokines, it has been reported that *Undaria pinnatifida* Sporophyll extract showed anti-inflammatory effect, and the ascidian shell GAG showed cell regeneration effect. Taking the foregoing into consideration, it deems that the *Undaria pinnatifida* Sporophyll extract and purified ascidian shell have excellent anti-inflammatory effect and skin regeneration effect rather than the mechanism of inhibiting cytokines.

TABLE 5

Effect of fucoidan for TNF-α at HaCaT cell culture

| Sample concentration (μg/mL) | | TNF-α production (%) |
|---|---|---|
| Control | | 100.0 ± 25.3 |
| Fucoidan | 0.1 | 50.1 ± 8.6 |
| | 1 | 42.3 ± 3.3 |
| | 10 | 27.9 ± 17.9 |
| | 100 | 24.1 ± 4.6 |
| | 200 | 26.7 ± 10.9 |
| GAG | 0.1 | 96.0 ± 1.7 |
| | 1 | 94.8 ± 0.0 |
| | 10 | 145.7 ± 37.1 |
| | 100 | 121.1 ± 4.9 |
| | 200 | 246.3 ± 6.6 |
| GAG:TSM (1:1) | 0.1 | 108.7 ± 6.1 |
| | 1 | 102.3 ± 7.2 |
| | 10 | 110.1 ± 21.1 |
| | 100 | 125.2 ± 4.7 |
| | 200 | 174.3 ± 5.6 |
| TF | 0.1 | 99.4 ± 3.3 |
| | 1 | 101.2 ± 5.6 |
| | 10 | 101.2 ± 2.4 |

TABLE 5-continued

Effect of fucoidan for TNF-α at HaCaT cell culture

| Sample concentration (μg/mL) | | TNF-α production (%) |
|---|---|---|
| | 100 | 104.1 ± 14.2 |
| | 200 | 137.4 ± 5.3 |
| GF | 0.1 | 101.2 ± 4.0 |
| | 1 | 102.3 ± 2.4 |
| | 10 | 92.6 ± 3.5 |
| | 100 | 126.1 ± 18.2 |
| | 200 | 114.0 ± 4.7 |
| GSM | 0.1 | 104.1 ± 9.5 |
| | 1 | 119.3 ± 1.4 |
| | 10 | 112.8 ± 3.7 |
| | 100 | 117.6 ± 2.1 |
| | 200 | 113.4 ± 6.2 |
| TSM | 0.1 | 94.8 ± 3.7 |
| | 1 | 108.7 ± 9.1 |
| | 10 | 113.4 ± 4.4 |
| | 100 | 105.2 ± 1.6 |
| | 200 | 110.5 ± 3.8 |

GAG: Glycosaminoglycans,
TF: Tongyeong *Undaria pinnatifida* Sporophyll fucoidan,
GF: Gijang *Undaria pinnatifida* Sporophyll fucoidan,
GSM: Gijang *Undaria pinnatifida* Sporophyll extract,
TSM: Tongyeong *Undaria pinnatifida* Sporophyll extract.

TABLE 6

Effect of fucoidan for IL-6 at HaCaT cell culture

| Sample concentration (μg/mL) | | IL-6 production (%) |
|---|---|---|
| Control | | 100.0 ± 0.3 |
| Fucoidan | 0.1 | 93.9 ± 0.3 |
| | 1 | 87.2 ± 0.4 |
| | 10 | 88.5 ± 0.7 |
| | 100 | 71.7 ± 0.4 |
| | 200 | 75.4 ± 0.3 |
| GAG | 0.1 | 129.0 ± 2.9 |
| | 1 | 157.9 ± 3.6 |
| | 10 | 296.2 ± 7.7 |
| | 100 | 321.3 ± 8.6 |
| | 200 | 428.3 ± 5.1 |
| GAG:TSM (1:1) | 0.1 | 270.8 ± 0.1 |
| | 1 | 99.3 ± 1.0 |
| | 10 | 116.9 ± 6.1 |
| | 100 | 173.0 ± 2.0 |
| | 200 | 213.1 ± 6.4 |
| TF | 0.1 | 109.6 ± 21.6 |
| | 1 | 111.1 ± 18.8 |
| | 10 | 107.4 ± 12.3 |
| | 100 | 113.9 ± 8.9 |
| | 200 | 130.3 ± 8.1 |
| GF | 0.1 | 110.6 ± 12.2 |
| | 1 | 112.8 ± 7.6 |
| | 10 | 118.0 ± 14.7 |
| | 100 | 136.1 ± 6.0 |
| | 200 | 162.2 ± 5.7 |
| GSM | 0.1 | 114.5 ± 3.8 |
| | 1 | 113.0 ± 6.8 |
| | 10 | 116.1 ± 10.9 |
| | 100 | 152.2 ± 13.3 |
| | 200 | 194.2 ± 0.7 |
| TSM | 0.1 | 125.5 ± 5.0 |
| | 1 | 117.3 ± 7.1 |
| | 10 | 108.6 ± 2.5 |
| | 100 | 131.5 ± 13.1 |
| | 200 | 151.2 ± 7.1 |

GAG: Glycosaminoglycans,
TF: Tongyeong *Undaria pinnatifida* Sporophyll fucoidan,
GF: Gijang *Undaria pinnatifida* Sporophyll fucoidan,
GSM: Gijang *Undaria pinnatifida* Sporophyll extract,
TSM: Tongyeong *Undaria pinnatifida* Sporophyll extract The foregoing exemplary embodiments and advantages are merely exemplary and are not to be construed as limiting the present invention. The present teaching can be readily applied to other types of devices. Also, the description of the exemplary embodiments is intended to be illustrative, and not to limit the scope of the claims, and many alternatives, modifications, and variations will be apparent to those skilled in the art.

What is claimed is:

1. A composition for alleviating atopic dermatitis comprising effective amounts of an *Undaria pinnatifida* Sporophyll extract and purified ascidian shell, wherein the ratio of the *Undaria pinnatifida* Sporophyll extract to the purified ascidian shell is 1:0.5 to 1:4 therein.

2. The composition of claim 1, wherein the *Undaria pinnatifida* Sporophyll extract is hot-water extract.

3. The composition of claim 2, wherein the *Undaria pinnatifida* Sporophyll extract contains fucoidan as an active ingredient.

4. The composition of claim 3, wherein the *Undaria pinnatifida* Sporophyll extract contains *Undaria pinnatifida* Sporophyll from Gijang or Tongyeong as a raw material.

5. The composition of claim 1, wherein the purified ascidian shell is ascidian shell dry powder.

6. The composition of claim 5, wherein the purified ascidian shell contains glycosaminoglycan as an active ingredient.

7. The composition of claim 1, wherein the composition is food composition, cosmetic composition, or pharmaceutical composition.

8. A method for manufacturing the composition according to claim 1 comprising:
   1) drying and crushing *Undaria pinnatifida* Sporophyll to obtain an *Undaria pinnatifida* Sporophyll powder; and drying and crushing ascidian shell to obtain a purified ascidian shell powder;
   2) boiling the *Undaria pinnatifida* Sporophyll powder in water preparation then centrifuging the water preparation to obtain an *Undaria pinnatifida* Sporophyll extract; and
   3) forming a mixture by heating and stirring the *Undaria pinnatifida* Sporophyll extract with the ascidian shell powder to obtain said composition,
   wherein the ratio of the *Undaria pinnatifida* Sporophyll extract to the purified ascidian shell powder is 1:0.5 to 1:4 within the mixture.

9. The method of claim 8, wherein in the step 1), drying includes natural dry in air for 1-5 days, and then drying in a dryer at temperature of 80-150° C. for 0.5 to 4 hours.

10. The method of claim 8, wherein in the step 2), water is deionized water.

11. The method of claim 8, wherein the mixture is heated at temperature of 40 to 80° C. for 10 to 120 minutes at step 3), and then stirred at a speed of 300 to 700 rpm for 0.5 to 3 hours.

12. A composition for alleviating atopic dermatitis comprising an effective amount of a mixture of *Undaria pinnatifida* Sporophyll extract and purified ascidian shell, whereby the composition is prepared by a method comprising:
   1) drying and crushing *Undaria pinnatifida* Sporophyll to obtain an *Undaria pinnatifida* Sporophyll powder; and drying and crushing ascidian shell to obtain a purified ascidian shell powder;
   2) boiling the *Undaria pinnatifida* Sporophyll powder in water to obtain an *Undaria pinnatifida* Sporophyll water preparation then centrifuging the water preparation to obtain an *Undaria pinnatifida* Sporophyll extract; and 3) forming a mixture by heating and stirring the *Undaria pinnatifida* Sporophyll extract with the purified ascidian shell powder to obtain said composition, wherein the ratio of the *Undaria pinnatifida* Sporophyll extract to the purified ascidian shell powder is 1:0.5 to 1:4 within the mixture.

13. A composition for alleviating atopic dermatitis comprising effective amounts of an *Undaria pinnatifida* Sporophyll extract which contains fucoidan as an active ingredient, and purified ascidian shell which contains glycosaminoglycan as an active ingredient, wherein the ratio of the *Undaria pinnatifida* Sporophyll extract to the purified ascidian shell is 1:0.5 to 1:4 therein.

* * * * *